United States Patent [19]

Traina

[11] Patent Number: 5,440,217

[45] Date of Patent: Aug. 8, 1995

[54] DRIVE MECHANISM FOR AUTOMATED FLOW MEASURING DEVICE

[75] Inventor: John E. Traina, Glenshaw, Pa.

[73] Assignee: United Sciences, Inc., Gibsonia, Pa.

[21] Appl. No.: 238,262

[22] Filed: May 4, 1994

[51] Int. Cl.⁶ .......................... G01F 1/00; G01N 1/22
[52] U.S. Cl. ..................................... 318/644; 73/861; 73/863; 318/51
[58] Field of Search ............... 318/644, 34, 35, 51, 318/466, 467, 468, 490; 73/23.2, 861, 861.65, 862.37, 863

[56] References Cited

U.S. PATENT DOCUMENTS

| | | |
|---|---|---|
| 3,819,330 | 6/1974 | Creighton . |
| 3,997,249 | 8/1976 | Wittig ................................ 73/212 |
| 4,161,883 | 7/1979 | Laird et al. . |
| 4,209,693 | 6/1980 | Fite et al. . |
| 4,561,288 | 12/1985 | Moenkhaus . |
| 4,974,455 | 12/1990 | McGowan et al. . |

FOREIGN PATENT DOCUMENTS 2231667 11/1990 United Kingdom .

OTHER PUBLICATIONS

Appendix A, Title 40, United States Code of Federal Procedure, Part 60, Chapter 1, EPA Methods 1 and 2, pp. 632–667.

*EPM Environmental*, Model 797, Diluting Stack Sampler Advertising Brochure.

Primary Examiner—Bentsu Ro
Attorney, Agent, or Firm—Buchanan Ingersoll; Lynn J. Alstadt

[57] ABSTRACT

A drive system for a probe of the type containing a first tubular housing within a second tubular housing which first tubular housing is advanced into and retracted from a conduit to take measurements of fluid within the conduit has a stepper motor for advancing the first tubular housing precisely controlled distances into and within the conduit. The stepper motor is connected to the first tubular housing through a friction drive roller which presses against the first tubular housing. Additionally, a rotational motor is connected to the outer tubular housing through a timing belt which extends around the second tubular housing. Sensors may be provided for measuring linear and rotational movement.

7 Claims, 6 Drawing Sheets

DRIVE MECHANISM FOR AUTOMATED FLOW MEASURING DEVICE

FIELD OF INVENTION

The invention relates to a drive mechanism for a probe used to measure stack gas velocity and volumetric flow rate which is useful for emissions monitoring.

BACKGROUND OF THE INVENTION

The federal government of the United States has promulgated test methods in 40 CFR Part 60, Appendix A for determining stack gas velocity and volumetric flow rate. If one knows the flow rate and has another monitor which measures the concentration of pollutants in a selected volume of fluid one can calculate the quantity of pollutants emitted over any selected time period. Accordingly, the test methods have been used in various ways, including the verification of the performance of continuous emission monitoring equipment required by other rules.

The United States has additional regulatory requirements in the form of 40 CFR, Parts 72 through 75 (acid rain reduction), which utilize the Appendix A methods. Some recent regulations now require many electric utilities to continuously measure emissions of specified pollutants on a mass per unit time basis. Adoption of these rules has put a new importance on the errors in both the continuous monitor and in the referenced test methods. The new regulations establish monetary value in the form of trading credits to a ton of $SO_2$ emissions. The value of such emissions is such that for large utilities as much as $1,000,000 per percent error in measured emissions may result.

The methods of Appendix A were introduced into law over 20 years ago. They, in general, use simple laboratory apparatus and manual techniques to make the various measurements. Unfortunately, the methods are error prone and tests under the same conditions often yield different results. There are many sources of error related to the care, speed and experience of the personnel performing the method as well as variability of the test hardware itself. In addition, the method makes compromises for practical reasons which further expand the margin of error. Over the years, the need to reduce the errors in these methods have been the subject of much discussion and little action.

Appendix A of Title 40 of the United States Code of Federal Regulations contains two methods for measuring flow which are used to determine compliance with emission regulations. These methods, known as EPA Methods 1 and 2, have gained prominence because they are used to determine the proper location, as well as to verify the performance of continuous measuring flow monitors. Errors in Method 2 data can be very costly to both the supplier of the monitor and the utility. The supplier is affected because the method can erroneously show the monitor is not meeting the performance guarantee. The utility is affected because the method is used to adjust the continuous monitor. If the method is in error, that error will directly cause an enormous high or low use of the utility's $SO_2$ allowance and $SO_2$ trading credits.

In performing the required testing methods the technician is required to make measurements at selected points within the stack. This is done by inserting a tube or probe into the stack through a port in the stack. Method 2 typically uses a type S (also called S-type) pitot tube made to specific dimensions. Method 2 refers to Method 1 to define the points at which the pitot tube must be placed in the stack or duct to be tested. After certain checks, the pitot tube is extended into the stack or duct to the points determined in Method 1. At each point the tester measures the static pressure in the stack and a differential pressure reading. The differential pressure reading is an average of several readings taken at that point. The person doing the test is expected to position the probe so that the pitot tube openings are at precisely the points required by Method 1. In addition, the tester is expected to align the probe with the direction of flow. Unfortunately, each tester is left to his own skill and resourcefulness to accomplish this task.

As the tester proceeds through the test procedure, he is asked to return again and again to the same measurement points with the same alignment of the probe. No position tolerance is provided in the method as an acceptable limit. Unfortunately, the tolerance required to limit the velocity determination to a specific level of error changes as a function of the stack and the type of flow patterns, as well as the skill of the tester.

The tester is often asked to place the pitot tube many feet into the stack or duct. It is not uncommon to see the end of the probe move considerably as a result of the turbulent gas flow. This movement can result in significant error. Such error is conjunctive to error caused by the fact that pressure is averaged and not the square root of the pressure. In addition to all this, the tester is asked to rotate the probe so as to obtain directional information about the flow at each measurement point. No tolerance limit is applied to this procedure.

There is a need for a drive mechanism which can insert the probe into the stack to predetermined positions. When so positioned the probe should not move during the test. The drive mechanism should also enable the tester to return the probe to any test position again and again.

Probes which are used in this environment typically are made of corrosion resistant metal because of the hot, corrosive environment in which they must operate. Frequently, particulates from the stack gas will adhere to the probe. Consequently, any drive system must be able to precisely position particulate encrusted probes.

Finally, the drive mechanism must be durable and not adversely affected by temperature changes and other environmental conditions found in power plants and other monitoring sites.

SUMMARY OF THE INVENTION

The present invention is a drive mechanism for a retractable probe. The drive mechanism includes a friction drive wheel. The probe also rests on at least one and preferably two alignment rollers mounted on Bellville washers. The alignment rollers are positioned near the drive wheel, preferably in the same plane. A roller assembly is provided to further support the probe in a housing. An encoder tracks the movement of the probe relative to the encoder to permit precise control of the probe's position. The drive system for the probe is controlled by a computer. The computer will calculate the points at which the probe is to be positioned for testing and will output signals to a stepper drive motor which will move the probe to each test point in the proper angular orientation.

The probe should have a mounting clamp which is used to attach the probe to the stack. The drive mechanism is a known distance from the clamp. Since the clamp is always attached to the stack at the same location relative to the stack it is easy to repeatedly position the distal end of the probe at any desired point in a transverse plane through the stack. A sensor measures the movement of the probe required to reach each position. A lap top computer can be used for controlling the drive system as well as receiving and storing the position of the probe based upon this sensed movement for each test sample taken. Hence, it is relatively easy to take samples at the same points at any subsequent time.

DESCRIPTION OF THE PREFERRED EMBODIMENTS

Figure 1:
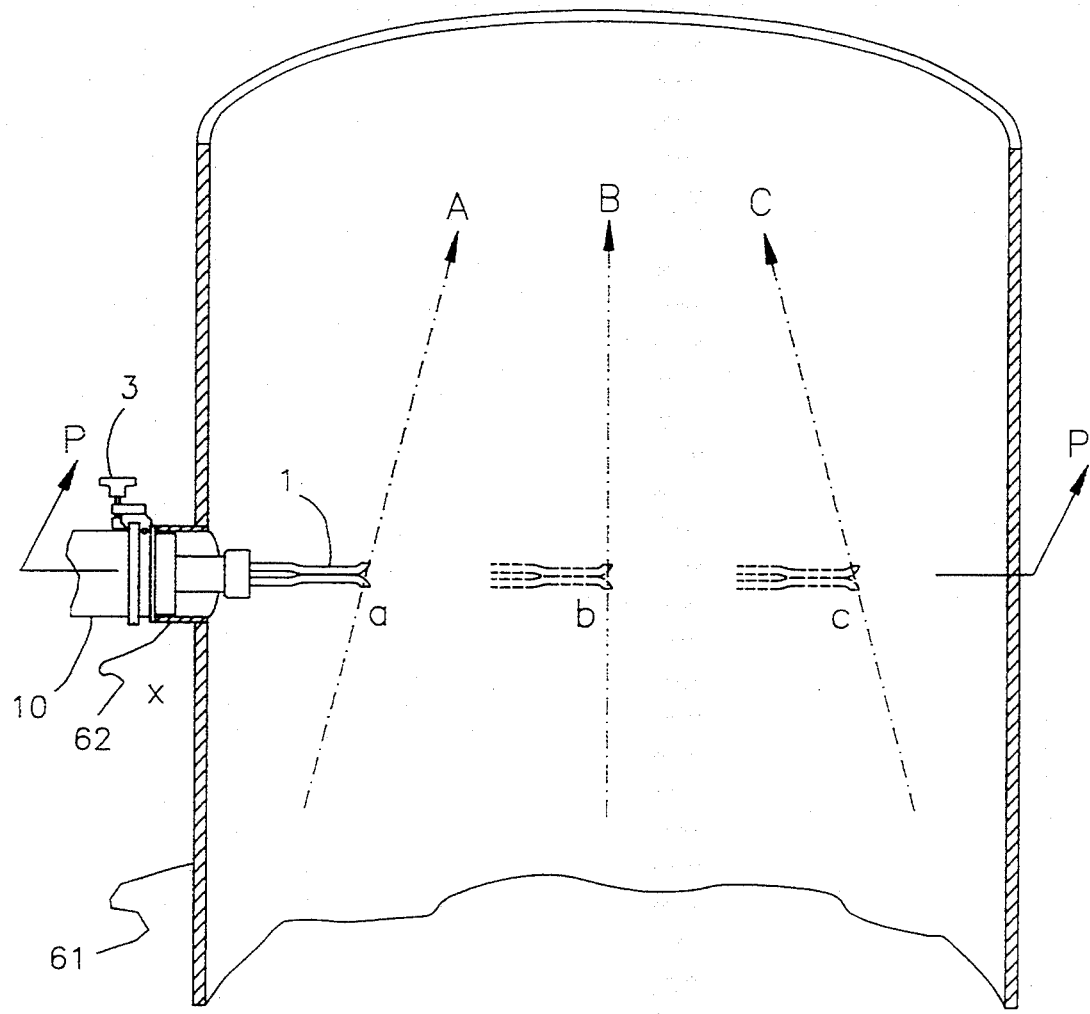
FIG. 1 is a perspective view of a section of a stack in which emission readings are to be taken.
Figure 2:
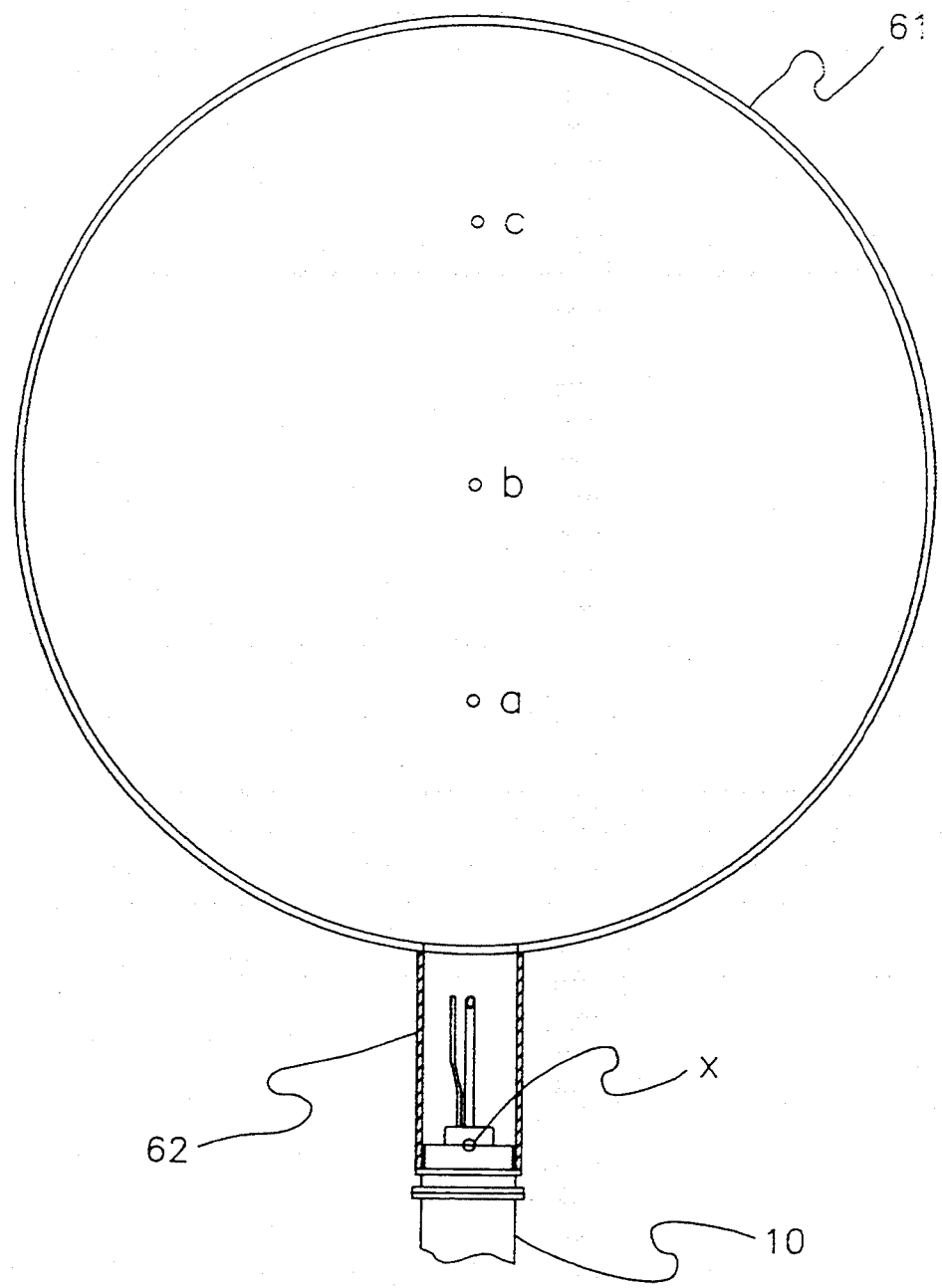
FIG. 2 is a diagram of a plane taken along line P—P through FIG. 1.

To illustrate the performance required from a sampling probe, consider the diagrams of FIGS. 1 and 2. A probe assembly 10 is mounted to a port 62 in a stack 61 in which emissions monitoring is performed. The probe assembly is held on the stack 61 by a clamp 3 having a set screw 63 (see FIG. 3) which attaches the probe assembly to the stack at point x. Assume that the test method requires readings to be taken at points a, b and c where vectors A, B and C pass through plane P. These vectors indicate possible directions of fluid flow within the conduit at the sampling points. These points are at known distances ax, bx and cx from point x. When the probe is properly mounted the tip of the probe initially will be at some known distance xy from point x. Therefore, the probe tip can be advanced to position a by advancing the probe a distance equal to ax-xy. To reach points b and c the probe must be moved distances (bx-xy) and (cx-xy) respectively. At each point the probe is rotated to find the flow direction shown by the vectors A, B and C in FIG. 1.

Figure 3:
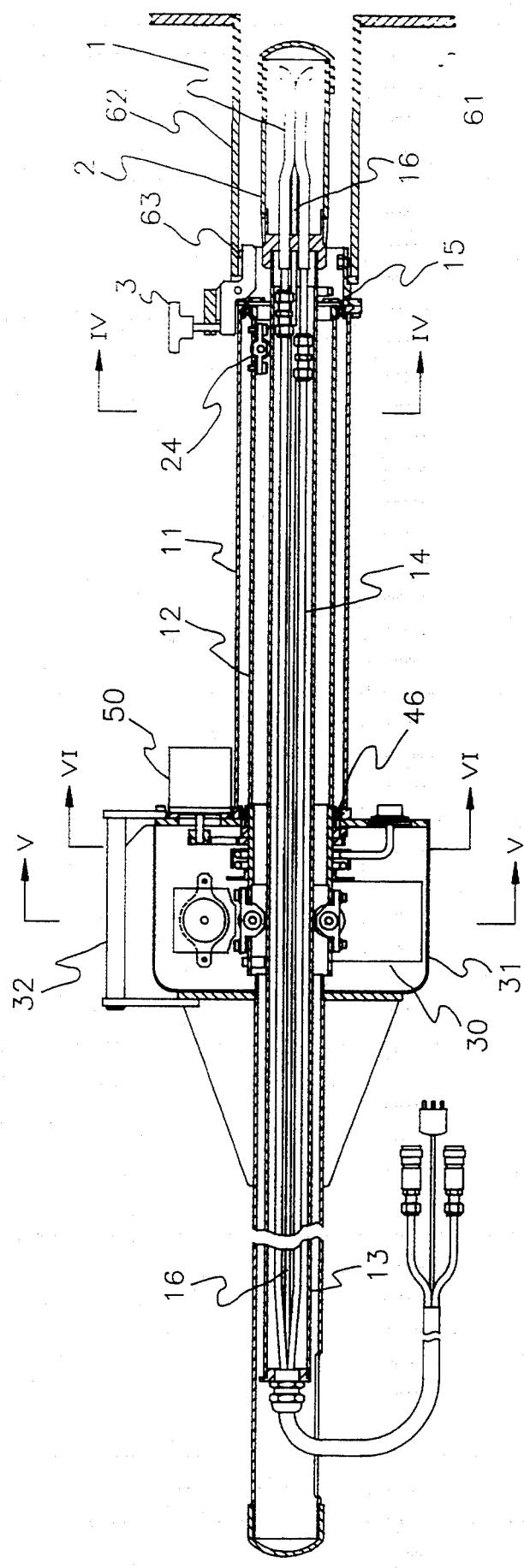
FIG. 3 is a side view partially in section of a present preferred probe assembly including the present preferred drive mechanism.
Figure 4:
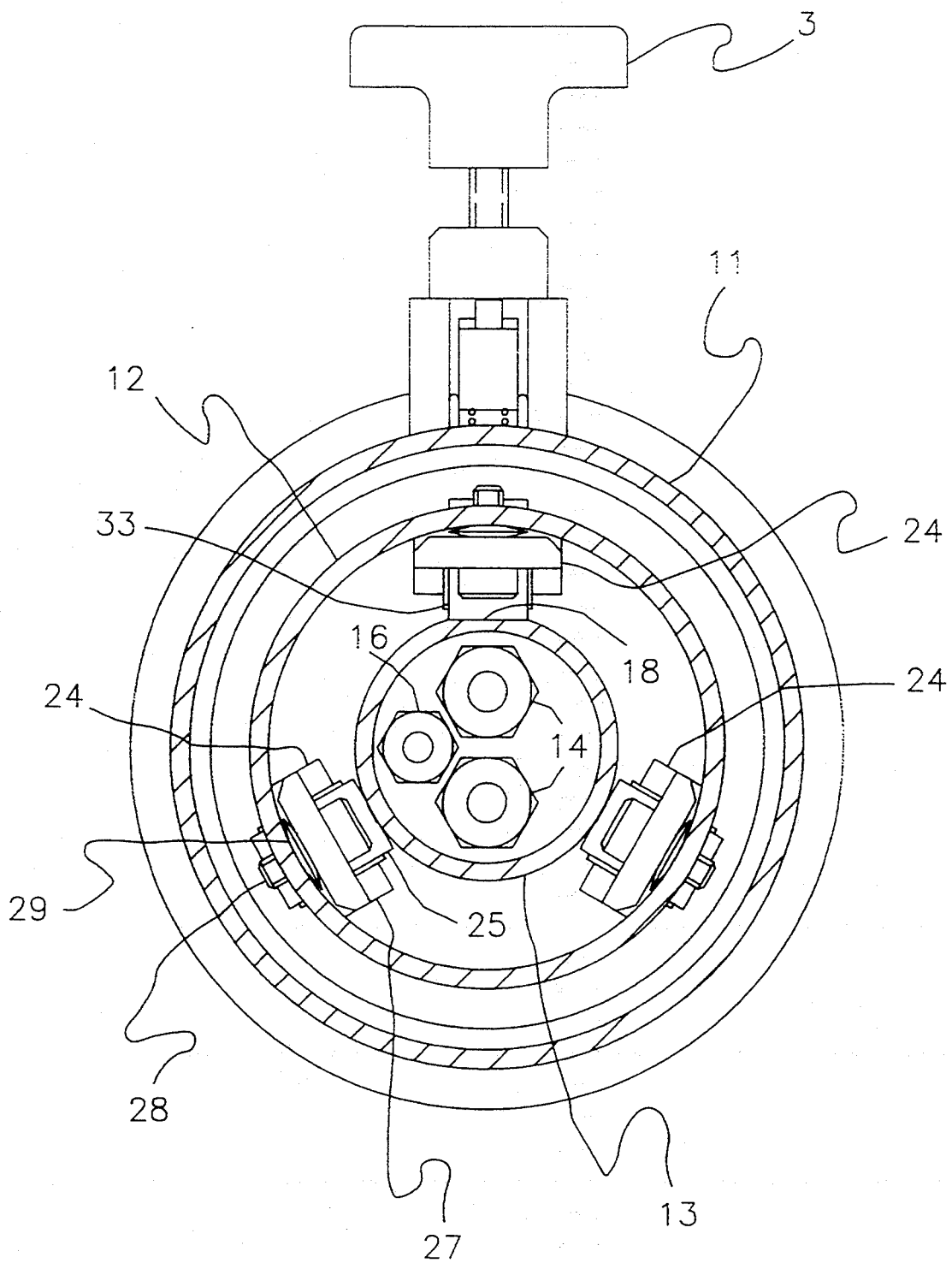
FIG. 4 is a sectional view taken along the line IV—IV of FIG. 3.

Referring to FIGS. 3 thru 6, my present preferred probe assembly 10 contains an outer tubular housing 11, middle tubular housing 12 and an inner tubular housing 13, all made of corrosion resistant metal. Two sample conduits 14 run through the housing 13. A pitot tube 1 is attached to the end of the conduits 14. I prefer to use a four foot conduits 14, but other lengths up to 12 feet are acceptable. A third conduit 16 is preferably provided containing a temperature probe. A cover 2 fits over the pitot tube for transport which cover is removed prior to the probe being inserted into the stack. A clamp assembly 3 with cone pointed set screw 63 and seal 15 allow the probe assembly 10 to be mounted in a port 62 on a stack or duct 61. The point of set screw 63 will be at point x in FIGS. 1 and 2. If desired bosses or other structures could be provided to assure that the probe assembly is always positioned in the same location when attached to the stack. Hence, tests can be repeated over time with the assurance that data is always being collected from the same points within the stack. As shown in FIGS. 3 and 4, the tubular inner housing rolls linearly on the roller assemblies 24 near the distal end of housing 12 and roller assemblies 26 near the drive motor. This housing may also rotate on the bearing assemblies 46.

The probes which are driven by the present drive system are sometimes used in environments which cause deposits to be formed on the exterior surface of the tubular housing 13 which extends into the duct. Even though that tubular housing is made of corrosion resistant alloys, pitting and cracking and surface damage may occur during use. Consequently, any drive system should not be affected by such deposits or surface damage in manner which skews or inhibits the precisely controlled movement of the tubular housing 13 and attached pitot tube.

Figure 5:
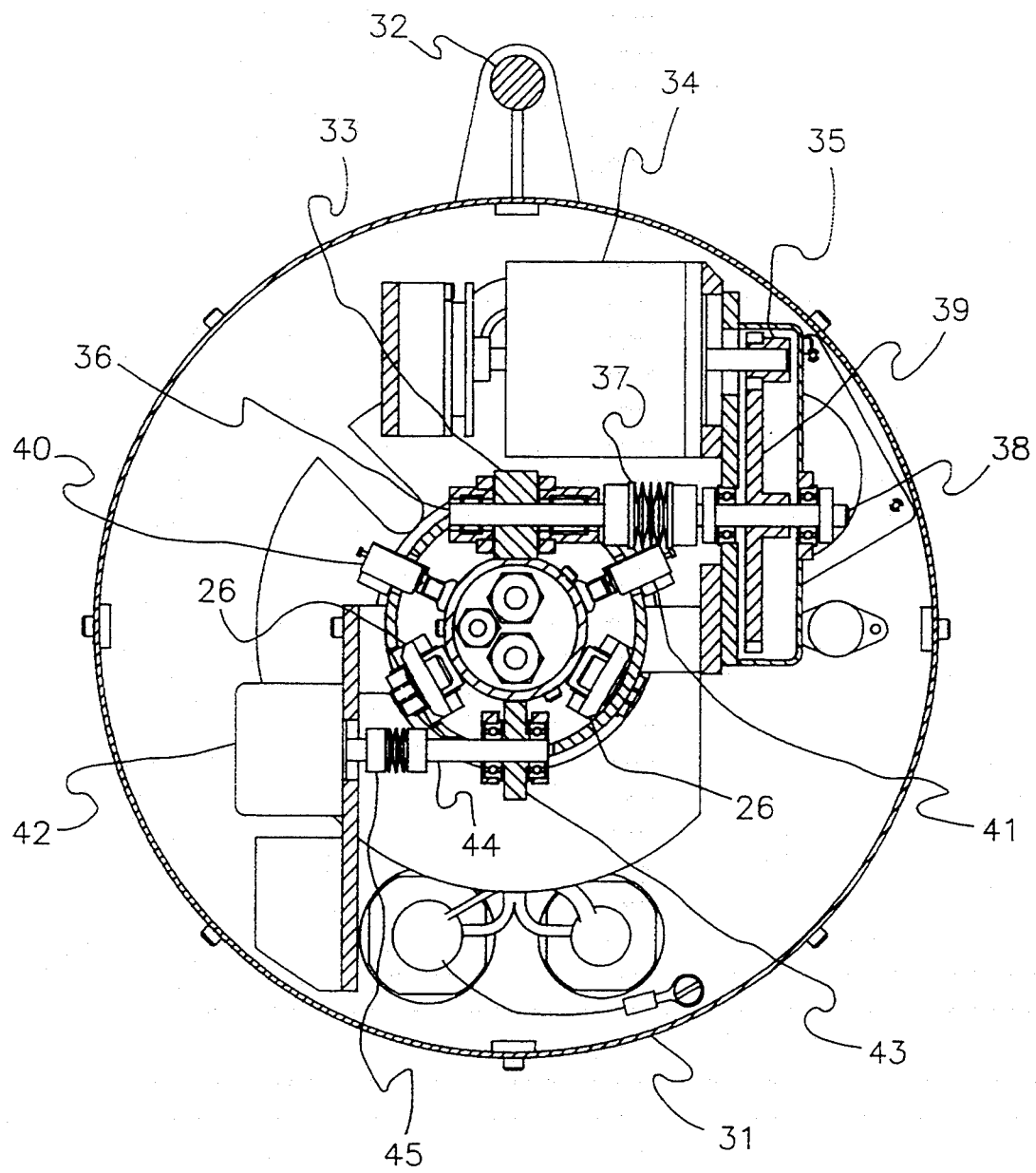
FIG. 5 is a sectional view taken along the line V—V of FIG. 3.

To assure that the tubular hosing remains properly oriented, I provide the roller assemblies 24 and 26 shown in FIGS. 4 and 5. Preferably three such assemblies 24 are equally spaced around the tubular housing 13 as shown in FIG. 4 or two such assemblies 26 are equally spaced from the drive roller 33 as shown in FIG. 5. As shown most clearly in FIG. 4, each assembly 24 and 26 has a roller 25 which engages inner tubular housing 13. The roller 25 is carried in a roller housing 27 which is attached to housing 12 by a nut and bolt or other attachment means 28. A plurality of Bellville washers are placed between roller housing 27 and tubular housing 12. The Bellville washers 29 force roller 25 against tubular housing 13. The force is strong enough so that deposits or irregularities on the surface of housing 13 will not cause the tubular housing to pitch or yaw which would result in movement of the pitot tube within the stack.

Figure 6:
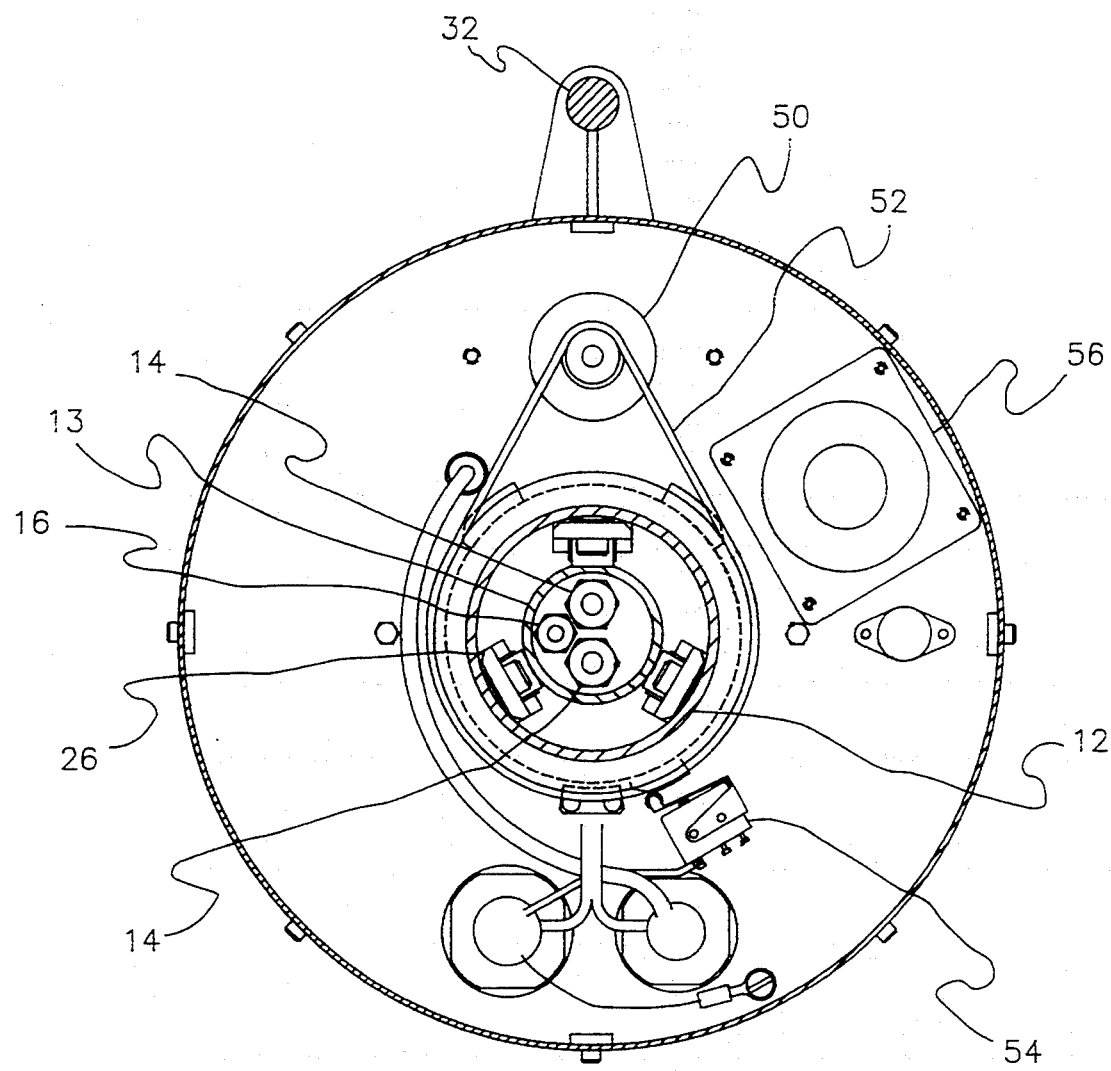
FIG. 6 is a sectional view taken along the line VI—VI of FIG. 3.

The drive system 30 is illustrated in FIGS. 3, 5 and 6 and is contained within housing 31. A carrying handle 32 extends above the housing. The inner tubular housing 13 is advanced and retracted by a friction drive which can be seen in FIG. 5. I prefer to provide a flat portion 18 extending longitudinally along tubular housing 13. A friction drive roller 33 engages the flat 18 of the tubular housing 13. The roller is mounted on shaft 36 which is coupled through coupling 37 to shaft 38. That shaft is driven by linear drive motor 34 connected to shaft 38 through gears 35 and 39. The linear driver motor is a stepper-type motor so that rotation of the shafts 36 and 38 can be precisely controlled. Furthermore, the shaft can be turned in either direction. Consequently, by precisely controlling the stepper motor 34, probe housing 13 can be advanced or retracted any desired distance. I prefer to provide limit switches 40 and 41 which are activated by projections (not shown) on housing 13. These projections are positioned to activate the switches when the probe is fully retracted and when the probe is fully extended.

I also prefer to provide an encoder device 42 to sense and measure the motion of the probe assembly 13. This encoder includes a roller 43 mounted on shaft 44. Roller 43 engages probe housing 13 and turns when the probe is extended and retracted. Movement of the probe housing 13 will cause corresponding movement of the roller 43 and attached shaft 44. That shaft 44 is coupled though coupling 45 to a device 42 which converts rotational movement of the shaft to electrical signals corresponding to that motion. Those signals are then sent to a computer (not shown) for use and storage. The encoder provides a check for movement of the probe. It should be apparent that one could rely simply on the linear drive system for precisely advancing and retracting the probe.

I also prefer to provide means for rotating housing 13. The rotational drive system is best shown in FIG. 6. A rotational drive motor 50 is provided within housing 31. A timing belt 52 encircles middle housing 12. Timing belts of the type used in the automotive industry are suitable for this purpose. The rotational drive motor is of the stepper-type which can be precisely controlled so that one can rotate the entire probe assembly in either direction by any desired amount. I also prefer to provide a sensor 54 which engages the timing belt 52 and measures actual movement of the belt and the housing 12 coupled thereto. In FIG. 6 one can also see the cables which run to the sensors and drive motors. I also prefer to provide a fan 56 within the housing to cool the motors and sensors and other equipment contained within the housing 31.

Operation of the probe is controlled by signals from a computer (not shown) to the motors 34 and 50. The computer will command the linear drive motor 34 to first extend the inner housing 13 and conduits 14 and 16 contained therein into the stack or duct so that the pitot tube 1 is at one of the desired locations.

Usually readings will be made by the system many times at each point. The probe is normally rotated both initially and after selected readings at each point. The probe will proceed from point to point repeating the measurements until the required number of points have been measured. Because the drive mechanism enables precise movement, the entire positioning of the probe can be activated after the probe has been attached to the stack. The computer will inform the tester to move the probe to the next port when the test is completed.

Because my probe assembly is clamped to the stack in a consistent manner and movement of the pitot tube is computer controlled, my system can provide consistent and repeatable results. Because my assembly is easy to install, there is little margin for human error. Moreover, a user friendly program can be provided to assure that all necessary data is collected and stored, thus eliminating uncertainties and errors from manual recording of "eyeball" data-taking.

Although I have described and shown certain present preferred embodiments of my invention, it should be distinctly understood that the invention is not limited thereto, but may be variously embodied within the scope of the following claims.

I claim:

1. A drive system for a probe of the type comprising in a first tubular housing contained within a second tubular housing which first tubular housing is advanced into and retracted from a conduit to take measurements of a fluid within the conduit and which second tubular housing is movably connected to an outer housing which can be connected to the conduit, comprising:
   a. a friction drive roller which engages the first tubular housing in a manner so that movement of the friction drive roller in one direction will cause the first tubular housing to advance and movement of the friction drive roller in an opposite direction will cause the first tubular housing to retract;
   b. a stepper motor connected to the friction drive roller and mounted on the second tubular housing;
   c. a rotational drive motor;
   d. a timing belt which extends from the rotational drive motor and encircles the second tubular housing for rotational movement of the second tubular housing and the stepper motor attached thereto; and
   e. at least one roller assembly attached to the second tubular housing and engaging the first tubular housing to guide movement of the first tubular housing relative to the second tubular housing.

2. The drive system of claim 1 also comprising at least one sensor for measuring longitudinal movement of the first tubular housing.

3. The drive system of claim 1 wherein the at least one roller assembly is comprised of a roller which engages the first tubular housing, a roller housing which holds the roller, means for attaching the roller housing to the second tubular housing and a plurality of Bellville washers positioned between the roller housing and the second tubular housing.

4. The drive system of claim 1 also comprising a drive system housing to which the rotational drive motor is attached and a fan attached to the drive system housing.

5. The drive system of claim 1 wherein there are two roller assemblies in plane passing through the friction drive roller, the two roller assemblies being equally spaced from the friction drive roller.

6. The drive system of claim 1 also comprising at least one limit switch connected to the stepper motor and engaging the first tubular housing.

7. The drive system of claim 1 also comprising a sensor adjacent the timing belt for measuring movement of the timing belt.

* * * * *